United States Patent [19]
Brady

[11] Patent Number: 4,726,358

[45] Date of Patent: Feb. 23, 1988

[54] MANIPULATIVE TREATMENT DEVICE HAVING PIVOTING LINKS BETWEEN BASE AND SUPPORTS

[75] Inventor: Alan C. Brady, Wodonga, Australia

[73] Assignee: World Products Pty. Limited, Wodonga, Australia

[21] Appl. No.: 863,412

[22] Filed: Apr. 9, 1986

[30] Foreign Application Priority Data

| | | | |
|---|---|---|---|
| Aug. 10, 1984 | [AU] | Australia | PG6501 |
| Aug. 1, 1985 | [WO] | PCT Int'l Appl. | PCT/AU85/00177 |

[51] Int. Cl.[4] .................. A61F 5/00; A61F 5/04

[52] U.S. Cl. .................. 128/72; 128/70

[58] Field of Search .................. 128/70, 71, 72, 73, 128/74; 269/325

[56] References Cited

U.S. PATENT DOCUMENTS

| | | | |
|---|---|---|---|
| 1,205,649 | 11/1916 | Miller | 128/72 |
| 1,448,477 | 3/1923 | Williams | 128/72 |
| 1,536,354 | 5/1924 | Phillips | 128/72 |
| 1,938,006 | 12/1933 | Blanchard | 128/74 |
| 2,002,349 | 5/1935 | Lundeen | 128/72 |
| 2,022,238 | 11/1935 | Hadley | 128/72 |
| 2,179,595 | 11/1939 | McManis | 128/72 |
| 2,451,607 | 10/1948 | Binash et al. | 128/72 |
| 2,715,557 | 8/1955 | Rock | 128/70 |
| 2,926,660 | 3/1960 | Thompson | 128/70 |
| 3,092,102 | 6/1963 | Thompson | 128/70 |
| 3,226,106 | 12/1965 | Johnson et al. | 128/72 |
| 4,004,305 | 1/1977 | Rubin | 5/345 |
| 4,230,100 | 10/1980 | Moon | 128/70 |
| 4,231,127 | 4/1980 | Bendell | 5/462 |
| 4,245,626 | 1/1981 | Paolino | 128/70 |
| 4,290,155 | 9/1987 | Hanson | 5/465 |
| 4,523,581 | 6/1985 | Ekholm | 128/70 |

FOREIGN PATENT DOCUMENTS

| | | | |
|---|---|---|---|
| 1108031 | 1/1956 | France | 128/70 |

*Primary Examiner*—Edgar S. Burr
*Assistant Examiner*—Tonya Lamb
*Attorney, Agent, or Firm*—Roylance, Abrams, Berdo & Goodman

[57] ABSTRACT

A device for manipulative therapy has a base and two support plates carried above the base by a plurality of links pivoted to the base and the respective plates. The links are disposed at angles such that the plates are movable in arcuate paths away from each other and towards the base. A control, mounted on the base beneath each plate has a spring biased spool engaging the respective plate. The spool has a groove engaged by a detent when the respective plate is in its uppermost position, requiring a predetermined force to be applied to the upper surface of the plate to produce downward, arcuate movement of that plate.

9 Claims, 8 Drawing Figures

MANIPULATIVE TREATMENT DEVICE HAVING PIVOTING LINKS BETWEEN BASE AND SUPPORTS

FIELD OF THE INVENTION

This invention relates to a device for manipulative treatment or therapy of humans or animals and relates particularly to a device to facilitate manipulative treatment of joints and the like.

Many physical disorders associated with joints, tendons, muscles and the like can be treated by manipulating the appropriate area of the body. Masseurs, chiropractors, medical practitioners, physiotherapists and others utilize manual manipulative treatment to correct many forms of physical disorders and to relieve pain associated with such disorders as well as pain arising from stress. Because most manipulative treatments are generally carried out manually, they may not be as effective or efficient as is desirable.

BACKGROUND OF THE INVENTION

It is well known to perform manipulative treatment on specially constructed tables, couches or the like which have various movable parts which are adjusted and locked in desired relative positions to facilitate the treatment. Thus, it is known to provide tables having head- and neck-rests, lumbar sections, pelvic sections, and other movable sections which can all be moved and locked in desired angular relationships so that the patient is supported on the table in a suitable attitude or posture for the desired treatment.

Such tables, however, play no part in the treatment itself other than acting as a patient support.

For various types of manipulative treatment, it is desirable that one part of a patients body be moved relative to another. This often requires the patient to be manually or mechanically supported or restrained to enable the appropriate manipulation to take place. Such support or restraining measures can, in some instances, be ineffective and, in other instances, can be distressful and uncomfortable to the patient.

BACKGROUND ART

Several forms of tables designed particularly for use by chiropractors, physiotherapists, masseurs, medical practitioners and the like have separate parts which are movable under the action of pneumatic, hydraulic or electrically induced forces during manipulative treatment to assist in that treatment. In one such table manufactured by Williams Manufacturing Co., Elgin, Ill., the various table sections such as the pelvic section, the lumbar section, etc., are movable relative to each other by pneumatic cylinders connected between the table frame and the individual sections. A foot pedal, or the like, operatively connected to the pneumatic system is operable by the manipulator i.e. a chiropractor, during manipulative treatment of a patient supported on the table sections.

Such tables, however, are relatively complex and, therefore, relatively difficult and expensive to manufacture.

Further, because of the complexity of the table, they are relatively difficult to use and can only be used by properly trained, professionally qualified practitioners. The tables also require a source of power and, because of their size and complexity, are not easily transportable.

Accordingly, it is desirable to provide apparatus to assist in manipulative treatment of patients which avoids at least some of the disadvantages of the known apparatus.

It is also desirable to provide apparatus which can be used by a variety of qualified or even non-qualified operators.

It is also desirable to provide a device which is relatively simple in construction and operation, and which is of a size which facilitates easy transportation.

SUMMARY OF THE INVENTION

According to one aspect of the invention there is provided a device for manipulative treatment comprising a base, at least two support members connected to the base, at least one of said support members being movable relative to the other support member from an initial, closely adjacent position to a spaced position, means to control said relative movement to a predetermined path, and means for returning said at least one support member from said spaced position to its initial position.

In a preferred form of the invention, both support members are movable relative to each other and to the base. It is also preferred that the means to control the relative movement comprises link members interconnecting the support members and the base and constraining the support members to move in an arc.

It is also preferred that the means for returning the at least one support member to its initial position comprises a return spring acting between the base and the respective support member. In one form of the invention, the return spring is adjustable to adjust the return spring pressure.

Preferably, means are provided to restrict relative movement of the respective support members. In a preferred form, the means comprise a spring loaded detent, which may be adjustable, and which acts to hold the respective support member in its initial, unmoved position until a predetermined force is applied to the support member causing movement past the detent.

Appropriate stops may be provided to restrict relative movement of the support members between predetermined limits. Such stop members may, if desired, be adjustable to vary the extent of such relative movement.

According to another aspect of the invention, there is provided a device for manipulative treatment comprising a base, a pair of plate members disposed in side-by-side relationship above said base, each said plate member being connected to the base by a plurality of link members pivoted to the base and to each plate member, said base, plate members and links being arranged so that the plate members, in a first position, are disposed with one edge of one plate member in closely adjacent proximity to an edge of the other plate member and the plates being movable relative to the base to a second position at which the said one edge of said one plate member is spaced from the said edge of the other plate member a predetermined distance, spring means associated with each plate member and biasing the respective plate members to the said first position, and control means resisting relative movement of said plate members until a predetermined force is applied thereto.

The plate members will normally be provided with shaped cushions on their upper surfaces to support appropriate parts of the body of the patient being treated.

On application of pressure to the patients body on the cushion plates, the plate members move to effect the desired manipulation.

The device of the present invention can be incorporated into a known table, such as the Thompson Terminal Point table (manufactured by Williams Manufacturing Co.) to either supplement the existing features and functions of the known table or to replace the existing mechanical, pneumatic, hydraulic and/or electrical operative table sections. When the device of the invention is incorporated into a table, manipulative treatment of parts of the patients body can be carried out simply by applying pressure to the body supported on the cushioned plates.

A manipulative treatment table may be constructed having a number of devices made in accordance with the present invention incorporated therein. Such an arrangement would avoid the need for any external power source to supply pneumatic, hydraulic or electrical power for operation of the movable portions of the table.

The operative movement of the support members of the invention may be controlled and varied between predetermined limits by varying the location of stops which limit the total movement of the support means and by varying the means which controls the amount of pressure required to cause movement of the support members and the means which returns the support members to their initial positions.

Many features and advantages of the invention will become apparent from the following description of an embodiment of the invention taken in conjunction with the accompanying drawings.

DESCRIPTION OF THE PREFERRED EMBODIMENT

Figure 2:
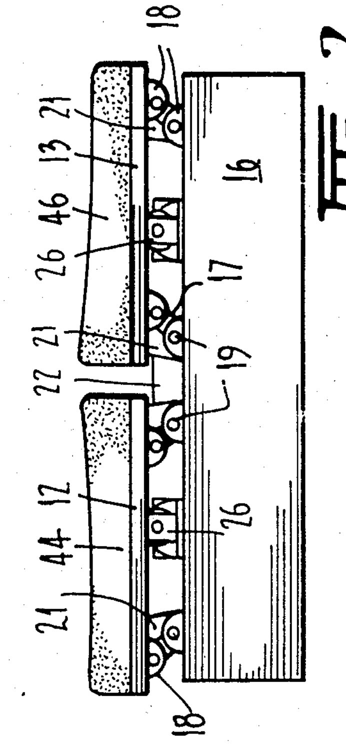
FIG. 2 is a side elevational view of the device of FIG. 1 but showing the cushion plates in an operated position.

Referring to the drawings, the embodiment illustrated comprises a manipulative device comprising a pair of cushion plates 12 and 13 mounted on a base plate 14 which is carried in a base housing 16. Each cushion plate 12 and 13 is connected to the base plate 14 by four (4) links 17. As shown more particularly in FIG. 5, each cushion plate 12 and 13 has four pairs of spaced link supports 18 and the base has eight pairs of spaced link supports, the respective links 17 being connected between the supports of each pair by pivot pins 19.

Figure 1:
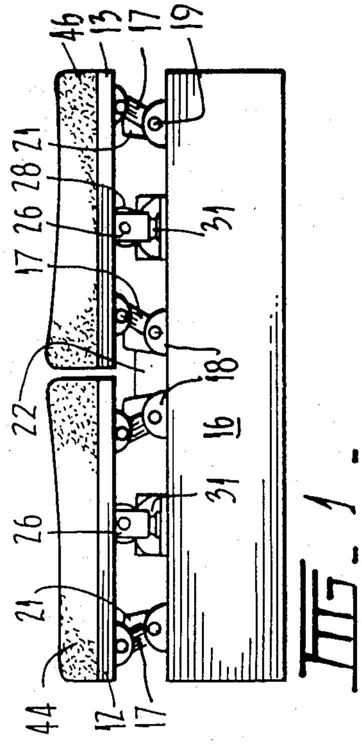
FIG. 1 is a side elevational view of one embodiment of the invention showing the cushion plates in a normal position.
Figure 4:
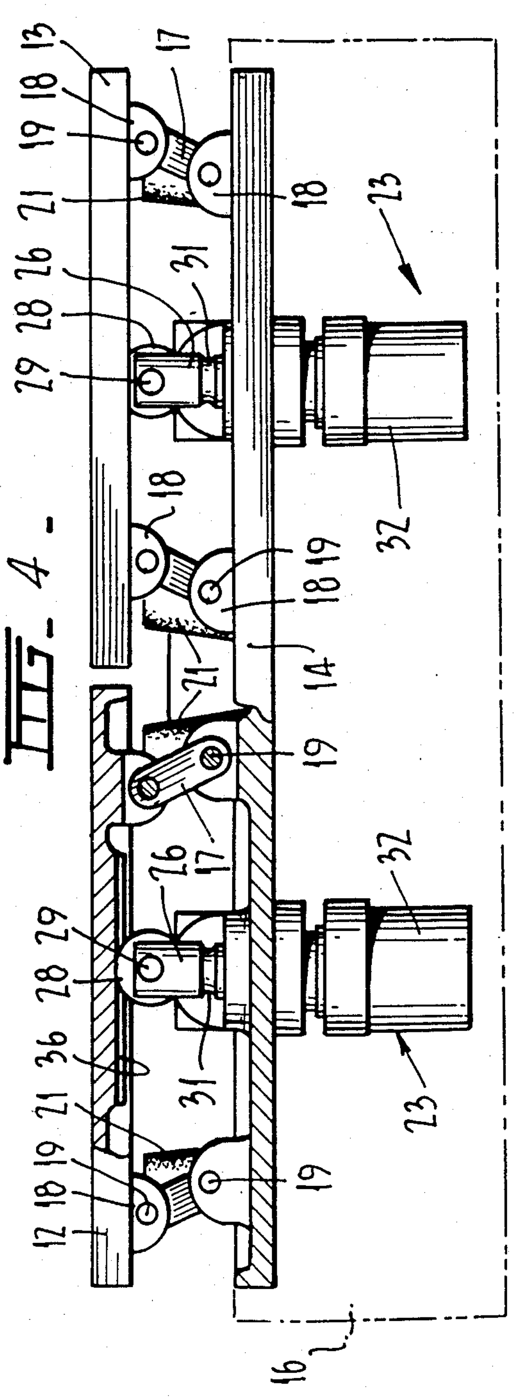
FIG. 4 is a part-sectional side elevational view in larger scale than FIG. 1.
Figure 3:
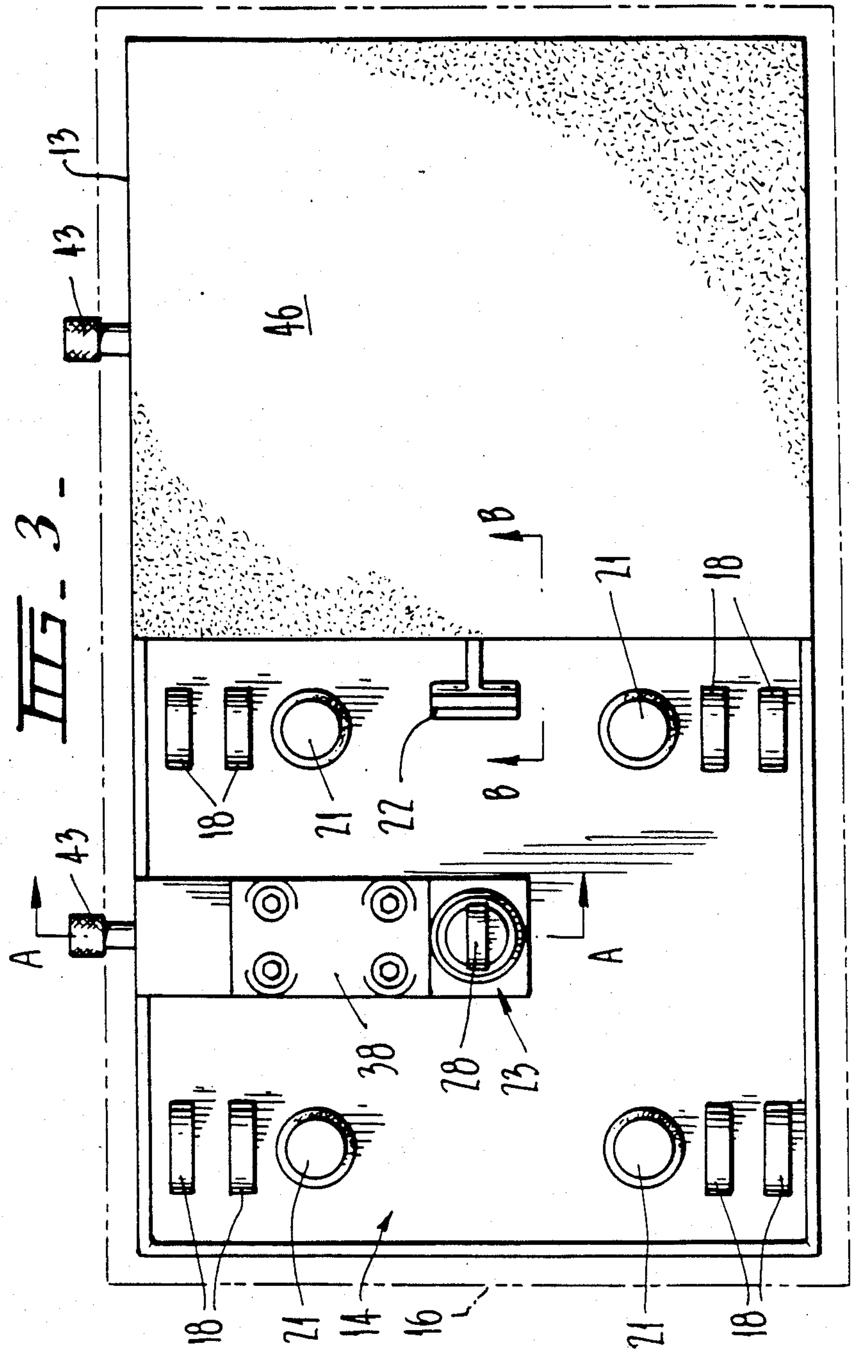
FIG. 3 is a plan view with one cushion plate removed for clarity.

As shown in FIGS. 1 and 4, when the cushion plates are in their normal, closely adjacent position, the links 17 carrying the cushion plate 12 extend upwardly from the base and at an angle away from the cushion plate 13 and the links supporting the cushion plate 13 also extend upward from the base and directed away from the cushion plate 12. The angular disposition of the links 17 and their pivotal mounting ensures that movement of the respective cushion plates 12 and 13 is generally arcuate towards the base plate 14 and away from each other.

Figure 6:
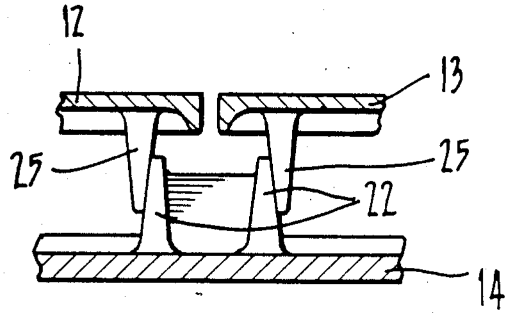
FIG. 6 is a detail part-sectional view taken along the lines B—B of FIG. 3.

The base plate 14 is provided with upwardly extending abutment members 21 which restrict the downward movement of the respective cushion plates 12 and 13. Each of the abutment members 21 has a resilient upper section of rubber or the like to absorb the shock of contact of the plates 12 and 13 with the abutment members 21. A pair of fixed stop members 22 (shown particularly in FIG. 6) extend upwardly from the base plate adjacent the centreline thereof. The stop members 22 are engageable by downwardly extending projections 25 on each cushion plate 12 and 13 to thereby restrict movement of the cushion plates 12 and 13 towards each other. Thus, each cushion plate 12, 13 is constrained for movement between the respective abutment members 21 and the fixed stop member 22.

Figure 7:
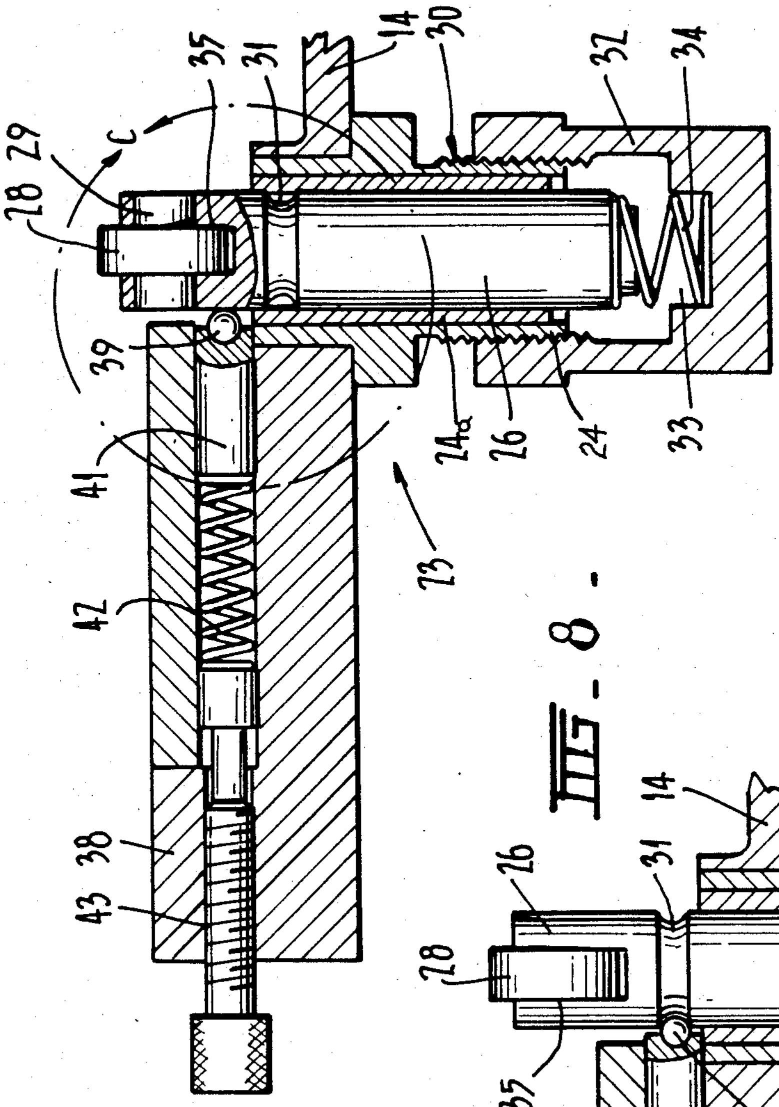
FIG. 7 is a sectional view taken along the line A—A of FIG. 3.
Figure 8:
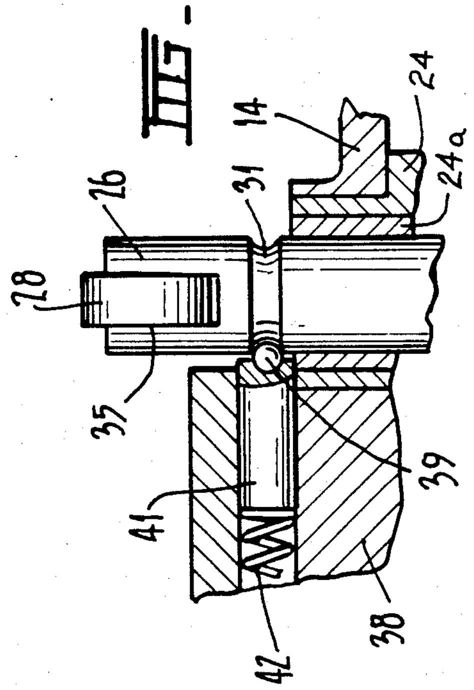
FIG. 8 is a detail view of the circled portion marked "C" of FIG. 7 showing the detent in the normal position.

The movement of each cushion plate 12, 13 is further controlled by respective separate controllers 23 which are more particularly shown in FIGS. 7 and 8. Each controller 23 is mounted on the base plate 14 and comprises a cylinder 24 with a cylinder liner 24*a*, the cylinder having its axis substantially perpendicular to the respective cushion plate 12, 13. The cylinder 24 houses an axially movable spool 26 formed at its upper end with a transverse slot 35 in which is mounted a bearing wheel 28 carried by an axle 29.

An annular, substantially semicircular shaped groove 31 is formed in the surface of the spool 26 at a predetermined distance below the bearing wheel 28.

The lower end of the cylinder 24 is screw threaded at 30 and a cap member 32 is threaded over the lower end of the cylinder, the cap member 32 having a recess 33 to receive a spring 34. The upper end of the spring 34 engages with the bottom end of the spool 26 to urge the spool 26 upwardly relative to the cylinder 24.

Figure 5:
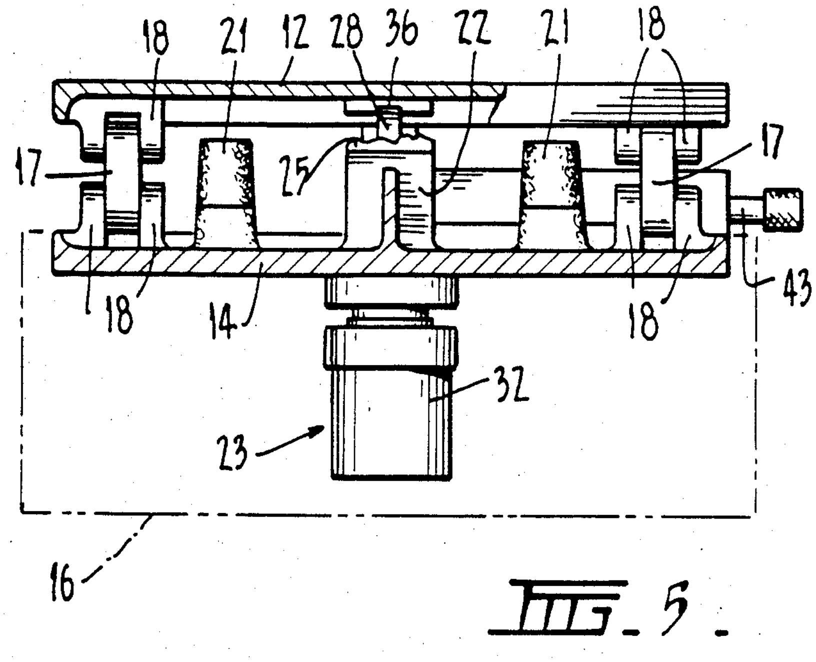
FIG. 5 is a part-sectional end elevational view.

Each cushion plate 12, 13 is formed with a groove 36 in its lower surface to receive the bearing wheel 28 (see FIG. 5).

A detent housing 38 is fixed relative to the cylinder 24 of each controller 23 and extends perpendicular to the axis thereof. The detent housing 38 carries a detent ball 39 mounted in a ball carrier 41 movable axially relative to the housing 38. A tension spring 42 mounted in the housing 38 provides a spring bias for the detent ball 39 towards the spool 26 and the bias is controlled by a threaded rod 43 extending through an outer, threaded portion of the housing 38. The detent ball 39 is adapted to engage in the annular groove 31 in the spool 26 when the groove 31 and detent ball 39 are aligned. This alignment coincides with the normal position of the cushion plates 12 and 13 as shown in FIG. 1. The engagement of the detent ball 39 in the annular groove 31 is more clearly shown in FIG. 8.

In operation of the device of this embodiment, a pair of cushions 44 and 46 of desired configuration and resilience are located on the cushion plates 12 and 13, preferably by locating holes in the cushion plates and corresponding pins extending from the respective cushions 44 and 46.

The thrust pressure necessary to cause movement of either of the cushion plates 12 and 13 relative to the base plate 14 is adjusted by means of the threaded rod 43 which adjusts the tension in the spring 42 and thus the pressure biasing the detent ball 39 into the annular groove 31.

A further pressure adjustment is made by the cap member 32 on the cylinder 24. The cap member is adjustable relative to the cylinder to tension the spring 34 which acts against downwardly movement of the respective cushion plates 12 and 13, and acts to return the cushion plates 12 and 13 to the normal position (FIG. 1).

If the device is to be used, for example, for manipulative treatment of the foot of a patient, the patient's foot is placed on the cushions 44 and 46 at the desired location determined by the operator. The operator applies a downward pressure to the foot, or to that part of the foot on one of the cushions 44, 46 and, provided the downward pressure applied is sufficient to overcome the thrust pressure of the detent ball 39 in the groove 31 of the controllers under each cushion plate 12 and 13, the plates 12 and 13 are caused to move downwardly relative to the base plate 14 and away from each other. This movement applies tension to the patient's foot on the cushions 44 and 46 for manipulative purposes. The downward movement of the base plates 12 and 13 is restricted by the resilient abutment members 21, which may be adjustable if desired for various applications of the device.

On release of pressure by the operator on the patient's foot, the return springs 34 in each controller move the respective spools 26 upwardly relative to the respective cylinders 24 to thereby return the cushion plates 12 and 13 to the normal position, the detent ball 39 reengaging in the groove 31.

As the cushion plates 12 and 13 move downwardly and outwardly relative to the base plate 14, the bearing wheels 28 in each controller roll in the groove 36 provided in the base of each cushion plate. Similarly, the pressure exerted by the return springs 34 acts through the spool 26 and the bearing wheel 28 of each controller. The groove 36 prevents relative rotation of the spool 26 about its axis and thus mis-alignment of the bearing wheel 28 in the groove 36.

In some cases of manipulative treatment, it may be desirable for only one of the cushion plates 12 and 13 to be movable relative to the other. For this purpose, the controllers 23 are separately adjustable by both adjustments of the threaded rod 43 and the cap member 32.

It will be seen that an important feature of the present invention is to provide a device which enables controlled relative movement to occur between supporting members so that one member moves relatively away from the other. While the provision of pivotal links 17 interconnecting the cushion plates 12 and 13 with the base plate 14 is a relatively simple means of achieving the desired result, it will be appreciated that other means may be utilized. Thus, the pivotal links may be replaced by angled ramps or other suitable means to control the relative movement of the cushion plates 12 and 13. Further, the plurality of links illustrated could be replaced by a single link and other guide means to control and guide the required relative movement.

Further, although two controllers 23 are shown in the preferred embodiment, it will be appreciated that a single controller may be utilized to control the movement of both cushion plates. However, it is preferred that a controller is provided for each plate to facilitate individual adjustment thereof.

While the controllers 23 used in the preferred embodiment provide substantial advantages in operation of the device, a simple form of device may be constructed and operated without such control. For this purpose, a simple return spring may be utilized to return the cushion plates to their normal position without provision for adjustment of the return force. Other forms of controllers may be utilized, as desired, such as, for example, a pneumatic or hydraulic system providing an adjustable, initial resistance to the downward thrust on the cushion plates 12 and 13 and having adjustable return pressure.

It will also be appreciated that the device of the invention may be constructed to provide either a fixed amount of relative movement between the cushion plates 12 and 13, or one of them, and the base plate 14, or adjustable relative movement which can be selectable or adjustable by the operator, depending on the parts of the body to be manipulated and the type of manipulation required. Thus, the resilient abutments may be of adjustable height above the base plate 14.

It has been found that the device of the present invention is particularly suitable for manipulative treatment of feet, hands, wrists, shoulders and elbows. It is envisaged that the device may be constructed for other manipulative treatments, and for this purpose, more than two support plates may be provided. The two or more support plates may be disposed at either a fixed or variable angle to each other to provide a relative movement between the plates at the desired angle.

The preferred embodiment described above may be of any convenient size commensurate with its intended use. It will be appreciated that the device is of a size to facilitate transportation, thus enabling an operator to take the device to the patient rather than, as is now required, requiring the patient to attend a particular location for manipulative treatment.

As previously indicated, the device may also be incorporated into the known forms of drop tables, such as those referred to above. Alternatively, the device of the invention may be mounted on a wall, to facilitate manipulative treatment of shoulder joints and the like, or in any other suitable location.

I claim:

1. A device for manipulative therapy, comprising:

a base;

two support members disposed in side-by-side relationship and spaced from the base, each support member being movably connected to the base by a plurality of links which extend angularly between pivotal mountings on the base and pivotal mountings on the respective support member, the links connected to the respective support members constraining movement thereof to a predetermined path, the links connecting one of the support members extending in a different direction to the links connecting the other support member so that the support members move away from each other as the support members move towards the base;

first stop means on the base for limiting movement of each said support member towards the base;

second stop means between the base and the support members for limiting movement of the support members towards each other; and control means on the base for each said support member for controlling relative movement towards the base of the respective support member, the control means including inhibiting means for inhibiting initial relative movement of the support means from a rest position, and including return means for returning the support members to the rest position after movement therefrom.

2. A device according to claim 1 wherein the links are all of equal length.

3. A device according to claim 1 wherein said first stop means comprises resilient abutments mounted on the base; and said second stop means comprises a rigid abutment on the base engageable by projections on the support members.

4. A device according to claim 1 wherein the links connected to each said support member are parallel.

5. A device according to claim 1 wherein said links constrain movement of said support members such that said support members move translationally.

6. A device according to claim 1 wherein each said link comprises an elongated member coupled adjacent opposite ends thereof to the respective pivotal mountings.

7. A device according to claim 1 wherein each said control means comprises a cylinder mounted in the base with an axis substantially perpendicular to the base, a spool axially movable in the cylinder, engaging means on the spool for contacting the respective support member and for permitting relative movement between the engaging means and the respective support member when the respective support member is moved from the rest position, and adjustable spring means biasing the spool into engagement with the respective support member.

8. A device according to claim 7 wherein said inhibiting means comprises an adjustable detent engaged with the spool, said detent including an annular groove in the spool, a detent ball engageable in the groove and a detent spring adjustably mounted to bias the detent ball against the spool and into the groove when the spool is in an upper position and the respective support member is in the rest position.

9. A drop table device for manipulative treatment, comprising:

a pair of plate members in side-by-side relationship, the plate members each being connected by four link members to a base, the link members being pivotally attached to the base and to the respective plate member and angularly disposed so that the plate members are arcuately movable relative to each other and the base from a closely spaced, rest position to a spaced apart, drop position;

a support cushion on an upper surface of each said plate member; and control means for each said plate member mounted on the base and including a cylinder, a spool axially movable in the cylinder, an adjustable return spring biasing the spool towards the respective plate member, an annular groove on the spool, a detent biased into engagement with the groove, a wheel mounted on an upper end of the spool and a groove formed in the respective plate member providing a track for the wheel.

* * * * *